United States Patent
Da Costa Pereira Rosa et al.

(10) Patent No.: US 11,008,327 B2
(45) Date of Patent: May 18, 2021

(54) PROCESSES FOR THE PREPARATION OF PHARMACEUTICALLY ACCEPTABLE SALTS OF (R)-PIRLINDOLE AND (S)-PIRLINDOLE

(71) Applicant: TECNIMEDE, SOCIEDADE TÉCNICO-MEDICINAL, SA, Sintra (PT)

(72) Inventors: Carla Patrícia Da Costa Pereira Rosa, Sintra (PT); João Carlos Ramos Damil, Sintra (PT); Ana Vanessa Cordeiro Simões, Sintra (PT); João Pedro Silva Serra, Sintra (PT)

(73) Assignee: TECNIMEDE, SOCIEDADE TÉCNICO-MEDICINAL, SA, Sintra (PT)

( * ) Notice: Subject to any disclaimer, the term of this patent is extended or adjusted under 35 U.S.C. 154(b) by 0 days.

(21) Appl. No.: 16/607,046

(22) PCT Filed: Apr. 20, 2018

(86) PCT No.: PCT/IB2018/052753
§ 371 (c)(1),
(2) Date: Oct. 21, 2019

(87) PCT Pub. No.: WO2018/193414
PCT Pub. Date: Oct. 25, 2018

(65) Prior Publication Data
US 2020/0131186 A1  Apr. 30, 2020

(30) Foreign Application Priority Data

Apr. 21, 2017 (PT) .......................................... 110037
Apr. 24, 2017 (EP) .................................... 17167851

(51) Int. Cl.
*C07D 487/22* (2006.01)
*C07D 487/04* (2006.01)

(52) U.S. Cl.
CPC ................................. *C07D 487/04* (2013.01)

(58) Field of Classification Search
CPC .................................................. C07D 487/22
USPC .................................................... 544/343
See application file for complete search history.

(56) References Cited

U.S. PATENT DOCUMENTS 3,288,860 A   11/1966   Lyness

FOREIGN PATENT DOCUMENTS

WO   2015171003   11/2015
WO   2015171005   11/2015

OTHER PUBLICATIONS

N I Andreeva et al: "Molecular Biological Problems of the Creation of Drugs and Study of the Mechanism of Their Action: Synthesis and Pharmacological Properties of Pyrazidole Enantiomers", Pharmaceutical Chemistry Journal, vol. 26, No. 5, 1992, pp. 365-369.
Aubry et al, "Synthesis and inhibition of cancer cell proliferation of (1,3')-bis-tetrahydroisoquinolines and piperazine systems," Biorganic Medicinal Chemistry Letters, vol. 17, 2007, pp. 2598-2602.
Bennasar et al, "Synthetic Efforts toward Akuammiline Alkaloids from Tetracyclic 6,7-Seco Derivatives," Journal of Organic Chemistry, vol. 61, No. 4, 1996, pp. 1239-1251.
A. I. Bokanov et al: "Synthesis of Heterocycles on the Basis of Iminotetrahydrocarbazoles. i. 3-Benzyl-8-Methyl-2-Oxo-2,3,3a,4,5,6-Hexahydro-IH-Pyrazino[3,2,l-j,k]", Chemistry of Heterocyclic Compounds, vol. 23, No. 12, Jan. 1, 1987 (Jan. 1, 1987), pp. 1311-1315.
Brady et al, "Halogenated Ketenes. 36. Reactions of Chloroketenes with Ketene Acetals," Journal of Organic Chemistry, vol. 46, No. 20, 1981, pp. 4047-4050.
Buckley et al, "Report on thermal reaction," Chemical & Engineering News, vol. 60, No. 28, 1982, p. 5.
Dewall et al., "Sodium Hydride and DMF," Chemical & Engineering News, vol. 60, No. 37, 1982, p. 5 and p. 43.
L.C. Cross and W. Klyne (collators), "Rules for the Nomenclature of Organic Chemistry. Section E: Stereochemistry (Recommendations 1974)," Pure & Applied Chemistry, vol. 45, 1976, pp. 11-30.
Roderick W R et al: "Derivatives of Piperazine. XXXV. Synthesis of 2-Phenylpiperazine and Some Derivatives", Journal of Medicinal Chemistry, American Chemical Society, Jan. 1, 1966 (Jan. 1, 1966), pp. 181-185, XP002290305, ISSN: 0022-2623, DOI: 10.1021/JM00320A005.
Rubiralta et al., "Studies on the Synthesis of the Indolo[2,3-a]quinolizidine System," Journal of Organic Chemistry, vol. 54, No. 23, 1989, pp. 5591-5597.
Saito et al., "Synthesis of Saframycins. XI. Synthetic Studies toward a Total Synthesis of Safracin A," Tetrahedron, vol. 51, No. 30, 1995, pp. 8213-8230.
P. Yu Ivanov et al: "New approach to the synthesis of pyrazidol", Pharmaceutical Chemistry Journal, vol. 21, No. 1, Jan. 1, 1987 (Jan. 1, 1987), US, pp. 62-65.
International Search Report and Written Opinion dated Jul. 6, 2018 corresponding to International Patent Application No. PCT/IB2018/052753; 10 pages.

*Primary Examiner* — Douglas M Willis
(74) *Attorney, Agent, or Firm* — Leason Ellis LLP

(57) ABSTRACT

The present disclosure relates to an improved process for the synthesis of piperazine ring, particularly for the preparation of heterocyclic compounds useful as intermediates in the synthesis of pyrazinocarbazoles such as the antidepressant Pirlindole. The process described is useful to prepare Pirlindole enantiomers, or a pharmaceutically accepted salt thereof.

40 Claims, No Drawings

PROCESSES FOR THE PREPARATION OF PHARMACEUTICALLY ACCEPTABLE SALTS OF (R)-PIRLINDOLE AND (S)-PIRLINDOLE

CROSS-REFERENCE TO RELATED APPLICATIONS

This is a U.S. National Phase Application under 35 U.S.C. § 371 of International Application No. PCT/IB2018/052753, filed Apr. 20, 2018, and claims priority to Portuguese (PT) Patent Application No. 110037, filed Apr. 21, 2017 and European Application No. 17167851.9, filed Apr. 24, 2017, all of which are hereby incorporated by reference in their respective entireties as if expressly set forth herein.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

Field of the Invention

The present disclosure relates to an improved process for the synthesis of piperazine ring, particularly for the preparation of heterocyclic compounds useful as intermediates in the synthesis of pyrazinocarbazoles such as the antidepressant Pirlindole. The process described is useful to prepare Pirlindole enantiomers, or a pharmaceutically accepted salts thereof.

Description of Related Art

Pirlindole hydrochloride is the compound represented in formula I

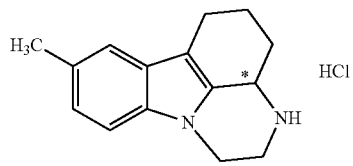

I

It is the common name of 8-methyl-2,3,3a,4,5,6-hexahydro-1H-pyrazino[3,2,1-jk]carbazole hydrochloride which is an active pharmaceutical ingredient marketed with the name Pyrazidol™. The compound is effective as an antidepressant agent.

Pirlindole chemical structure belongs to the pyrazinocarbazole group. It is composed of one stereogenic centre which anticipate the existence of two enantiomers, the (R)-Pirlindole of formula II and the (S)-Pirlindole of formula III.

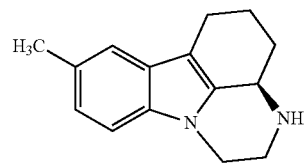

II

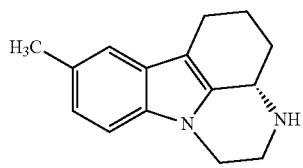

III

Although Pirlindole pharmacological data and the clinical use were performed on the racemate, recently there have been increasing interest in the pharmacological profile of each enantiomer (WO 2015/171005 A1).

The document WO 2015/171003A1 (Tecnimede group) filed 9 May 2014 discloses a resolution of racemic pirlindole into optically active pirlindole. The Resolution-Racemization-Recycle (RRR) synthesis described involves derivatization by preparation of pairs of diastereomers in the form of salts from an optically active organic acid. These diastereomers can be separated by conventional techniques such as crystallisation. Although it is a very efficient procedure to prepare laboratorial scale or pre-clinical batch of (R)- or (S)-Pirlindole, it is not economically convenient at an industrial scale because the process relies on Pirlindole racemate as the starting material.

Processes to prepare Pirlindole involve the formation of a piperazine ring. The state of the art discloses different processes for piperazine ring formation but they are generally a multistep approach, and they are hampered by low yields, expensive reagents, or are reported as unsuccessful (Roderick et al. *Journal of Medicinal Chemistry* 1966, 9, 181-185).

The first asymmetric synthesis of Pirlindole enantiomers described by Andreeva et al. (*Pharmaceutical Chemistry* 1992, 26, 365-369) discloses a one-step process to prepare pyrazinocarbazole piperazine ring system from a tetrahydrocarbazole-amine. The process discloses a very low yield (23.8%) and employs the use of sodium hydride (NaH) in the presence of dimethyl sulfoxide (DMSO) or dimethyl formamide (DMF), both conditions described as generating exothermic decomposition that can cause reaction ignition or reaction thermal runaway.

The mixture of sodium hydride with DMSO generates dimsyl anion. This anion is very often used in laboratory scale, but because it is unstable its use on large scale should be under specific precautions. The dimsyl anion decomposition is exothermic. It is reported that dimsyl anion decomposition starts even at 20° C., and above 40° C. it decomposes at an appreciable rate (Lyness et al. U.S. Pat. No. 3,288,860).

The mixture of DMF and sodium hydride is reported in Sax & Lewis's Dangerous Properties of Industrial Materials to give a violent reaction with ignition above 50° C. Buckey et al., (Chemical & Engineering News, 1982, 60(28), 5) describes the thermal runaway of a pilot plant reactor containing sodium hydride and DMF from 50° C. Accelerated Rate Calorimetry (ARC) tests showed exothermic activity as low as 26° C. Similar behaviour was also seen with DMA. De Wall et al. (Chem. Eng. News, 1982, 60(37), 5) reports a similar incident, wherein runaway started at 40° C., and rose 100° C. in less than 10 minutes, boiling off most of the DMF.

An alternative process for the preparation of a piperazine ring system of a pyrazinocarbazole derivative can involve the formation of a lactam ring in a three steps approach:
1. N-acylation reaction;
2. intramolecular indole acetamide cyclisation to afford a lactam ring;
3. lactam reduction.

Intramolecular indole chloroacetamide cyclization to yield a lactam ring has been described by Bokanov et al. (*Pharmaceutical Chemistry Journal* 1988, 23, 12, 1311-1315) particularly in the non-enantioselective synthesis of pyrazinocarbazolone derivatives. Bokanov et al. did not describe the lactam reduction into a piperazine ring.

Intramolecular indole chloroacetamide cyclization to yield a lactam ring has also been described both by Rubiralta et al. (*Journal of Organic Chemistry* 1989, 54, 23, 5591-5597) and Bennasar, et al. (*Journal of Organic Chemistry* 1996, 61, 4, 1239-1251), as an unexpected outcome of a photocyclization reaction. The lactam conversion was low (<11% yield).

Lactam reduction of a pyrazinone into piperazine ring systems is disclosed both by Aubry et al. (*Biorganic Medicinal Chemistry Letters* 2007, 17, 2598-2602) and Saito et al. (*Tetrahedron* 1995, 51, 30, 8213-8230) in the total synthesis of alkaloid natural products.

There exists the need for improved processes for the preparation of piperazine ring derivatives in particular enantioselective processes for the preparation of pyrazinocarbazole intermediates precursors of Pirlindole enantiomers compounds of formula II and III.

These facts are disclosed in order to illustrate the technical problem addressed by the present disclosure.

BRIEF SUMMARY OF THE INVENTION

The process disclosed herein provides an improved process for the preparation of piperazine ring, particularly for the preparation of pyrazinocarbazoles, such as Pirlindole enantiomers II and III or pharmaceutically acceptable salts thereof.

The present disclosure relates to the transformation of compound of formula VI ((S)-6-methyl-N—((S)-1-phenylethyl)-2,3,4,9-tetrahydro-1H-carbazol-1-amine) into compound of formula IV (S)-8-methyl-3-((S)-1-phenylethyl)-3a,4,5,6-tetrahydro-1H-pyrazino[3,2,1-jk]carbazol-2(3H)-one), which can be prepared in a two-step, one-reaction vessel approach that involves the N-acylation and intramolecular indole acetamide cyclisation. N-acylation reaction is under biphasic alkaline conditions; the unreacted compound of formula VI is recovered by filtration in the form of hydrochloride salt and is re-used in the N-acetylation step. The intramolecular indole acetamide cyclisation is also implemented in a biphasic alkaline system under phase transfer catalyst conditions. The amount of phase transfer catalyst used was very reduced, in particular less than 0.1 equivalents in relation to compound of formula X, more in particular 0.01 equivalents.

The present disclosure relates to a process for the synthesis of pirlindole enantiomers of formula II or III

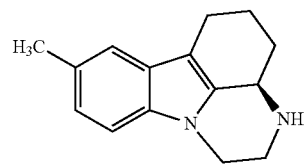

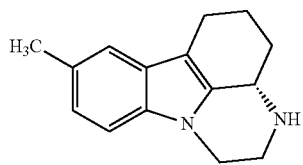

or a pharmaceutically accepted salt thereof, comprising the following steps:
reacting compound of formula VI (S)-6-methyl-N—((S)-1-phenylethyl)-2,3,4,9-tetrahydro-1H-carbazol-1-amine or compound of formula VIII (R)-6-methyl-N—((R)-1-phenylethyl)-2,3,4,9-tetrahydro-1H-carbazol-1-amine,

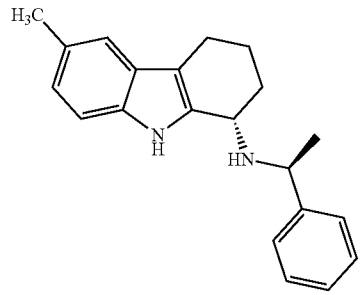

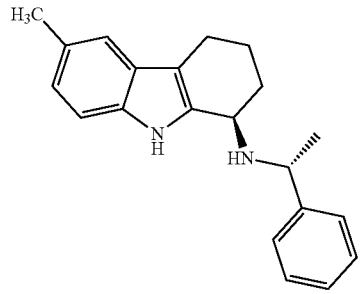

and an acylating compound of formula XII

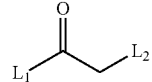

wherein
L1 is a leaving group selected from —Br, —Cl, —OTs,-OMs, OH, —OR$_1$, —OCOR$_1$ or imidazole
R$_1$ is hydrogen, C$_1$-C$_6$ alkyl chain or an aryl, in a first aprotic solvent, in the presence of an alkaline agent to yield compound of formula X, 2-substituted N—((S)-6-methyl-2,3,4,9-tetrahydro-1H-carbazol-1-yl)-N—((S)-1-phenylethyl)acetamide or compound of formula XI, 2-substituted N—((R)-6-methyl-2,3,4,9-tetrahydro-1H-carbazol-1-yl)-N—((R)-1-phenylethyl)acetamide

X

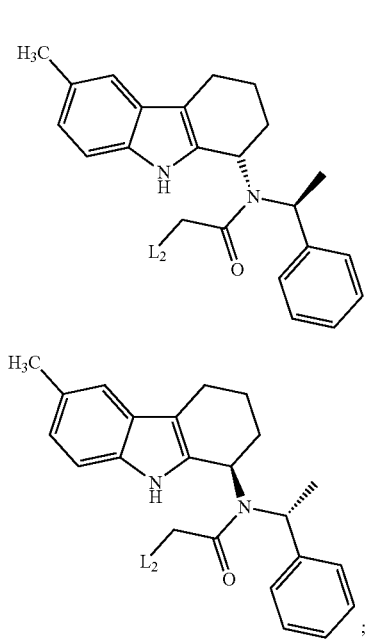

XI intramolecular indole acetamide cyclisation of compound of formula X or compound of formula XI
wherein $L_2$ is a leaving group selected from —Br, —Cl, —I,-OTs,-OMs, —OH, —OR$_1$, in a second aprotic solvent, in the presence of an alkaline agent and a phase transfer catalyst to yield compound of formula IV, (S)-8-methyl-3-((S)-1-phenylethyl)-3a,4,5,6-tetrahydro-1H-pyrazino[3,2,1-jk]carbazol-2(3H)-one or compound of formula XIV (R)-8-methyl-3-((R)-1-phenylethyl)-3a,4,5,6-tetrahydro-1H-pyrazino[3,2,1-jk]carbazol-2(3H)-one

IV

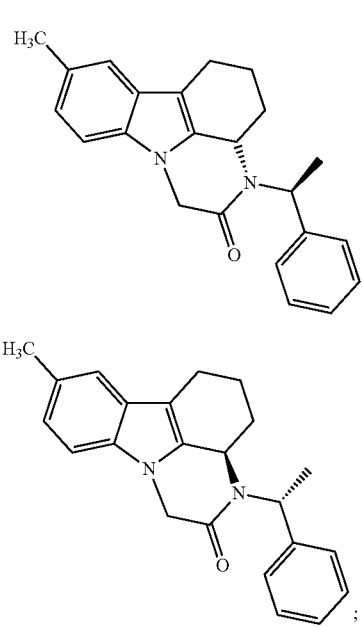

XIV reducing the lactam ring of compound of formula IV or compound of formula XIV into compound of formula V or compound of formula IX, respectively, in a third aprotic solvent, in the presence of a reducing agent

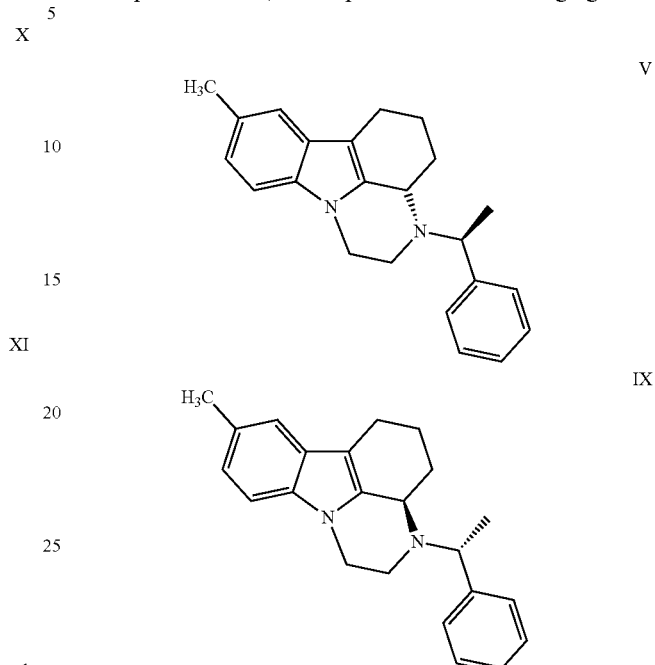

and catalytic hydrogenolysis or acidic phenyl cleavage to yield of Pirlindole enantiomers of formula II or III or its pharmaceutically acceptable salts.

In an embodiment, the alkaline agent may be selected from a tertiary organic amine, for example pyridine or trimethylamine; a carbonate of an alkali metal salt, for example potassium carbonate or sodium carbonate; a hydrogencarbonate of an alkali metal salt, for example sodium hydrogencarbonate or potassium hydrogencarbonate; or an alkali metal salt, for example sodium hydroxide or potassium hydroxide.

In an embodiment, the alkaline agent is sodium hydroxide, in particular the alkaline agent is a 50% (w/v) aqueous solution of sodium hydroxide.

In an embodiment, the first aprotic solvent and the second aprotic solvent may be independently selected from chloroform, dichloromethane, dimethoxyethane, diethyl ether or toluene, preferably the first aprotic solvent may be toluene; the second aprotic solvent may also be toluene.

In an embodiment, the third aprotic solvent may be selected from dichloromethane, tetrahydrofuran, diethyl ether or toluene, preferably it may be tetrahydrofuran.

In an embodiment, $L_1$ may be —Cl.
In an embodiment, $L_2$ may be —Cl.
In an embodiment, $R_1$ may be $C_1$-$C_6$ alkyl chain.
In an embodiment, the molar ratio between alkaline agent:compound formula VI or VIII:compound formula XII may be between 1:1:1 and 15:1:4, preferably 10:1:3.

The process according to any of the previous claims wherein the molar ratio between the alkaline agent:compound of formula X or XI:phase transfer catalyst may be between 1:1:0.005 and 15:1:0.1, preferably 10:1:0.01.

In an embodiment, the molar ratio between the reducing agent:compound formula IV or compound formula XIV, may be between 1:1 and 4:1, preferably 3.3:1.

In an embodiment, the reducing agent may be selected from lithium aluminium hydride (LiAlH$_4$), diisobutylaluminium hydride (Dibal-H), aluminium hydride (AlH$_3$), sodium bis(2-methoxyethoxy)aluminium hydride or borane tetrahydrofuran (THF) complex, preferably sodium bis(2-methoxyethoxy)aluminium hydride.

In an embodiment, the phase transfer catalyst may be selected from quaternary ammonium halogen salts such as tetrabutyl ammonium bromide, tetraethyl ammonium bromide, benzyltributyl ammonium bromide, tetrabutyl ammonium hydrogen sulphate and benzyltributyl ammonium chloride.

In an embodiment, the acylating compound XII is chloroacetyl chloride.

In an embodiment, the phase transfer catalyst is tetrabutyl ammonium bromide.

In an embodiment, the pharmaceutically acceptable salt of Pirlindole enantiomer III or II may be acetate salt, hydrochloride salt, hydrobromide salt, mandelate salt, citrate salt, succinate salt, tartrate salt, malonate salt, maleate salt, methanesulfonate salt, lactate salt, ethanesulfonate salt, glutamate salt, phosphate salt.

In an embodiment, the catalytic hydrogenolysis may be carried out at 20-70° C., preferably 50° C.

In an embodiment, the catalytic hydrogenolysis may be carried out for 2-8 hours, preferably 5 hours.

In an embodiment, the catalytic hydrogenolysis may be carried out with an hydrogen pressure between 500 KPa-2000 KPa (5-20 bar), more preferably 700 KPa (7 bar).

In an embodiment, the catalytic hydrogenolysis is carried out at 20-70° C., preferably for 2-8 hours and with an hydrogen pressure between 500 KPa-2000 KPa (5-20 bar).

In an embodiment, the catalytic hydrogenolysis may be carried out with an acidified solvent mixture selected from ethylacetate, dimethyl formamide, methanol, ethanol, isopropanol and dichloromethane, preferably the acidified solvent mixture is a mixture of a protic solvent with dichloromethane, more preferably methanol with dichloromethane.

In an embodiment, the pyrazinocarbazole derivative compound of formula V was obtained through selective reduction of the lactam ring of compound of formula IV to afford a piperazine ring.

In an embodiment, the catalytic hydrogenolysis of compound of formula V obtained by this process produces high purity crude compound of formula III ((S)-pirlindole) requiring simple purification steps, as no basification is necessary.

BRIEF DESCRIPTION OF THE SEVERAL VIEWS OF THE DRAWINGS

Not Applicable.

DETAILED DESCRIPTION OF THE INVENTION

The present disclosure provides a process for the synthesis of piperazine rings, particularly for the preparation of heterocyclic compounds useful as intermediates in the synthesis of pyrazinocarbazoles. These intermediates are suitable for use in the asymmetric synthesis of Pirlindole enantiomers which are readily convertible to the corresponding acid salts.

The present disclosure relates to the N-acylation and intramolecular cyclization reaction to afford pyrazinocarbazolone derivative of formula IV, (S)-8-methyl-3-((S)-1-phenylethyl)-3a,4,5,6-tetrahydro-1H-pyrazino[3,2,1-jk]carbazol-2(3H)-one

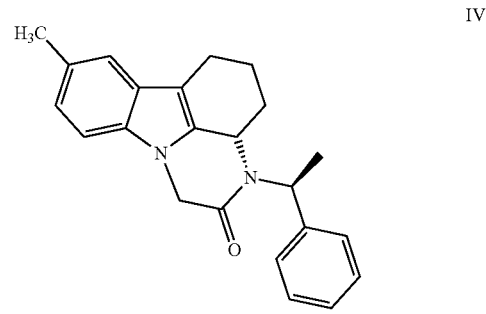

IV

Another aspect refers to the selective reduction of compound of formula IV into piperazine derivative compound of formula V, (S)-8-methyl-3-((S)-1-phenylethyl)-2,3,3a,4,5,6-hexahydro-1H-pyrazino[3,2,1-jk]carbazole

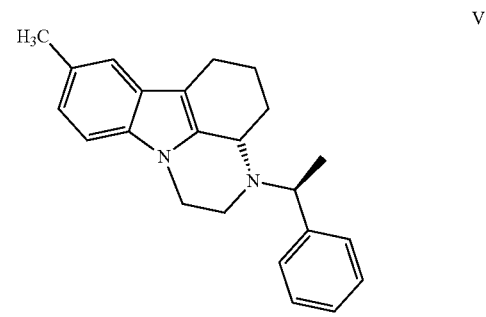

V which can be subjected to catalytic hydrogenolysis to afford (S)-Pirlindole compound of formula III.

In an embodiment, the compound of formula VI, (S)-6-methyl-N—((S)-1-phenylethyl)-2,3,4,9-tetrahydro-1H-carbazol-1-amine

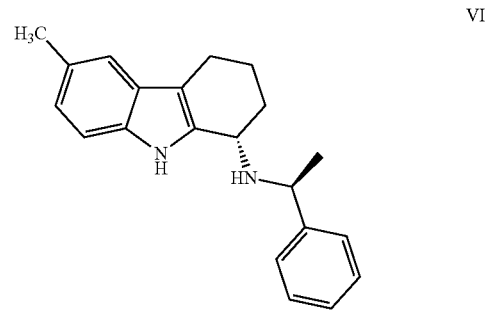 [SMILES: Cc1ccc2[nH]c3c(c2c1)CCC[C@@H]3N[C@@H](C)c1ccccc1]

VI is an intermediate in the synthesis of pyrazinocarbazole V and can be prepared in two steps:

1-condensation of compound of formula VII, 6-methyl-2,3,4,9-tetrahydro-1H-carbazol-1-one

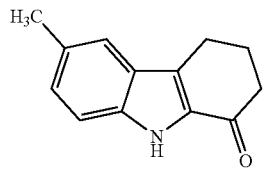

VII with chiral auxiliary (S)-(−)-α-methylbenzylamine, followed by:

2-stereoselective reduction with sodium borohydride.

In an embodiment, the process of the present disclosure is the preparation of (R)-Pirlindole of formula II, wherein the enantiomer of compound formula VI, (R)-6-methyl-N—((R)-1-phenylethyl)-2,3,4,9-tetrahydro-1H-carbazol-1-amine (formula VIII)

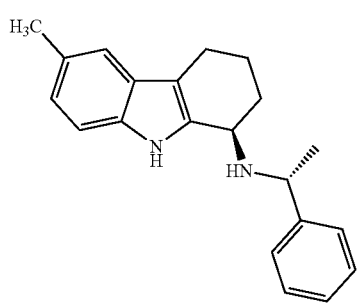

VIII is obtained from condensation of compound formula VII with (R)-(+)-α-methylbenzylamine.

In an embodiment, the compound of formula VIII can be acylated, cyclized and reduced to yield compound of formula IX, (R)-8-methyl-3-((R)-1-phenylethyl)-2,3,3a,4,5,6-hexahydro-1H-pyrazino[3,2,1-jk]carbazole

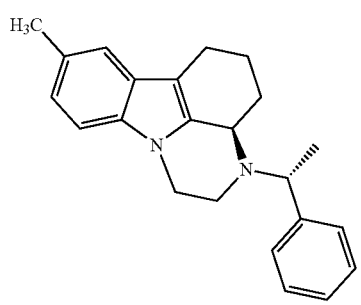

IX which can be subjected to catalytic hydrogenolysis to afford (R)-Pirlindole compound of formula II.

Another aspect of the present disclosure relates to the N-acylation reaction of compound of formula VI generating compound of formula X, 2-substituted N—((S)-6-methyl-2,3,4,9-tetrahydro-1H-carbazol-1-yl)-N—((S)-1-phenylethyl)acetamide

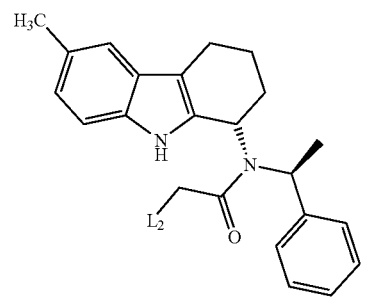

X

Another aspect of the present disclosure relates to the N-acylation reaction of compound of formula VIII generating compound of formula XI, 2-substituted N—((R)-6-methyl-2,3,4,9-tetrahydro-1H-carbazol-1-yl)-N—((R)-1-phenylethyl)acetamide

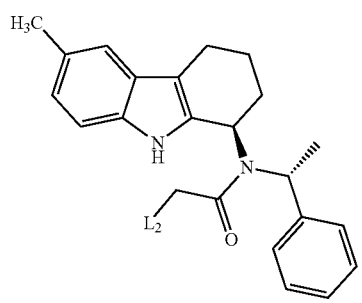

XI

In an embodiment, the compound of formula VI or compound of formula VIII are reacted with compound of formula XII wherein $L_1$ and $L_2$ are leaving groups in a suitable solvent and in the presence of a suitable alkaline agent.

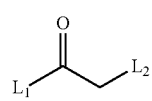

XII

Examples of leaving groups include, but are not limited to, halogens such as —Br, —Cl, or sulfonic alcohols such as —OTs and —OMs, or hydroxyl group —OH, or alkoxy groups such as —$OR_1$, or anhydrides of a carboxylic acid such as —$OCOR_1$, or imidazole. Preferably $L_1$ is —Cl. $R_1$ is hydrogen, $C_1$-$C_6$ alkyl or aryl.

Compound of formula XII can also be represented by ketene of formula XIII

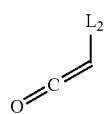

XIII

Ketene compound of formula XIII can be obtained commercially or it can be prepared in situ from compound of formula XII. The state of the art discloses procedures to prepare ketene from acylating agent XII (e.g. Brady et al. *Journal of Organic Chemistry* 1981, vol. 46, 20 p. 4047-4050).

In an embodiment, the suitable solvent for the conversion of compound of formula VI into compound of formula X according to the disclosure is selected from, but not limited to aprotic solvents such as chloroform, dichloromethane (DCM), dimethoxyethane (DME), diethyl ether or toluene.

In an embodiment and to obtain even better results, the above-mentioned suitable solvent is preferably toluene.

In an embodiment, the suitable alkaline agent according to the disclosure is selected from, but not limited to a tertiary organic amines such as pyridine or triethylamine, or a carbonate or hydrogencarbonate of an alkali metal salt such as potassium carbonate or sodium carbonate or sodium hydrogencarbonate or potassium hydrogencarbonate or an alkali metal salt such as sodium hydroxide (NaOH) and potassium hydroxide (KOH).

In an embodiment and to obtain even better results, preferably the alkaline agent is sodium hydroxide, even more preferably the alkaline agent is a 50% (w/v) aqueous solution of sodium hydroxide.

In an embodiment and to obtain even better results, preferably the molar ratio between the acylation reaction components alkaline agent, compound formula VI, and compound formula XII is between 1:1:1 and 15:1:4, more preferably it is 10:1:3.

In an embodiment and to obtain even better results, preferably the molar ratio between the acylation reaction components alkaline agent, compound formula VIII, and compound formula XII is between 1:1:1 and 15:1:4, more preferably it is 10:1:3.

In an embodiment, the reaction occurs at a temperature between −10° C. and 20° C., preferably between 0-5° C. for 30 minutes to 10 hours, more preferably 4 hours.

In an embodiment, preferably compounds of formula XII is an acyl halide.

Another embodiment of the present disclosure relates to the intramolecular indole acetamide cyclisation of compound of formula X into compound of formula IV, wherein $L_2$ is a leaving group in a suitable solvent and in the presence of a suitable alkaline agent and a phase transfer catalyst.

Another embodiment of the present disclosure relates to the intramolecular indole acetamide cyclisation of compound of formula XI into compound of formula XIV, (R)-8-methyl-3-((R)-1-phenylethyl)-3a,4,5,6-tetrahydro-1H-pyrazino[3,2,1-jk]carbazol-2(3H)-one

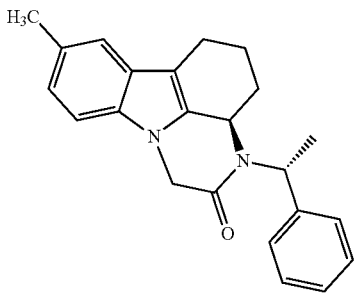

XIV wherein $L_2$ is a leaving group in a suitable solvent and in the presence of a suitable alkaline agent and a phase transfer catalyst.

Examples of leaving groups include, but are not limited to, halogens such as —Br, —Cl, —I or sulfonic alcohols such as —OTs and —OMs or alkoxy groups such as —$OR_1$. Preferably $L_2$ is —Cl. $R_1$ is hydrogen, $C_1$-$C_6$ alkyl or aryl.

In an embodiment, the compound of formula XII is preferably chloroacetyl chloride.

In an embodiment, the suitable alkaline agent according to the disclosure is selected from, but not limited to, a tertiary organic amines such as pyridine or trimethylamine, or a carbonate or hydrogencarbonate of an alkali metal salt such as potassium carbonate or sodium carbonate or sodium hydrogencarbonate or potassium hydrogencarbonate or an alkali metal salt such as sodium hydroxide and potassium hydroxide.

In an embodiment and to obtain even better results, the alkaline agent is preferably sodium hydroxide, even more preferably the alkaline agent is a 50% (w/v) aqueous solution of sodium hydroxide.

In an embodiment, the suitable solvent according to the disclosure is selected from, but not limited to aprotic solvents such as chloroform, dichloromethane, dimethoxyethane, diethyl ether or toluene. Preferably the solvent is toluene.

In an embodiment, the suitable phase transfer catalyst according to the disclosure is selected from, but not limited to the group comprising the quaternary ammonium salts such as tetrabutyl ammonium bromide, tetraethyl ammonium bromide, benzyltributyl ammonium bromide, tetrabutyl ammonium hydrogen sulphate and benzyltributyl ammonium chloride.

In an embodiment and to obtain even better results, preferably the phase transfer catalyst is tetrabutyl ammonium bromide.

In an embodiment and to obtain even better results, the molar ratio is preferably between the cyclization reaction components alkaline agent, compound of formula X, and phase transfer catalyst is between 1:1:0.005 and 15:1:0.1. More preferably it is 10:1:0.01.

In an embodiment and to obtain even better results, the molar ratio is preferably between the cyclization reaction components alkaline agent, compound of formula XI, and phase transfer catalyst is between 1:1:0.005 and 15:1:0.1. More preferably it is 10:1:0.01.

In an embodiment, the cyclization reaction occurs at a temperature between 20° C. and 100° C., preferably at 65° C. for 30 minutes to 2 hours, more preferably 1 hour.

Another embodiment of the present disclosure relates to the selective lactam reduction reaction of compound of formula IV into compound of formula V in a suitable solvent, in particular an aprotic solvent, and with an appropriate reducing agent.

Another embodiment of the present disclosure relates to the selective lactam reduction reaction of compound of formula XIV into compound of formula IX in a suitable solvent, in particular an aprotic solvent, and with an appropriate reducing agent.

Accordingly to the present disclosure an appropriate reducing agent include, but are not limited to organolithium reagents such as lithium aluminium hydride ($LiAlH_4$), diisobutylaluminium hydride (Dibal-H), aluminium hydride ($AlH_3$) or sodium bis(2-methoxyethoxy)aluminium hydride, but also organoboron reagent or complex such as borane THF complex.

In an embodiment and to obtain even better results, preferably the reducing agent is sodium bis(2-methoxyethoxy)aluminium hydride.

In an embodiment, the suitable solvent for the preparation of compound formula V or compound of formula IX according to the present disclosure, include but is not limited to an aprotic solvent such as dichloromethane, tetrahydrofuran, diethylether and toluene.

In an embodiment and to obtain even better results, the aprotic solvent is preferably tetrahydrofuran.

In an embodiment, preferably the molar ratio between the lactam reduction components reducing agent:compound formula IV is between 1:1 and 4:1, more preferably it is 3.3:1.

In an embodiment, preferably the molar ratio between the lactam reduction components reducing agent:compound formula XIV is between 1:1 and 4:1, more preferably it is 3.3:1.

In an embodiment, the lactam reduction occurs at a temperature between room temperature and 100° C., preferentially at 50° C. for 30 minutes to 5 h, preferably for 30 minutes to 3 h, more preferably 1 h.

In an embodiment, intermediate V obtained by a process according to the disclosure can be subjected to catalytic hydrogenolysis or acidic phenyl ethyl cleavage. Catalytic hydrogenolysis in acidified organic solvent mixture affords compound of formula III (S)-Pirlindole. Catalytic hydrogenolysis is under hydrogen pressure or under transfer hydrogenolysis conditions.

In an embodiment, intermediate IX obtained by a process according to the disclosure can be subjected to catalytic hydrogenolysis or acidic phenyl ethyl cleavage. Catalytic hydrogenolysis in acidified organic solvent mixture affords compound of formula III (R)-Pirlindole. Catalytic hydrogenolysis is under hydrogen pressure or under transfer hydrogenolysis conditions.

In an embodiment, preferably the acidic phenyl ethyl cleavage is conducted by an acidic cleavage agent such as boron or aluminium trihalide. More preferably the acidic cleavage agent is boron trichloride, boron tribromide or aluminium chloride.

In an embodiment, preferably the catalytic hydrogenolysis uses heterogeneous catalyst and occurs under hydrogen pressure. Preferably the heterogeneous catalyst is palladium on charcoal. More preferably the heterogeneous catalyst will have a palladium content of approximately 3.2 mol %.

In an embodiment, preferably the hydrogen pressure for catalytic hydrogenolysis is between 500 KPa-2000 KPa (5-20 bar), more preferably 700 KPa (7 bar).

In an embodiment, preferably the temperature for catalytic hydrogenolysis can be between 20-70° C. More preferably the temperature is 50° C.

In an embodiment, preferably the catalytic hydrogenolysis lasts for a period of 2 to 8 hours, more preferably 5 hours.

In an embodiment, suitable catalytic hydrogenolysis acidified solvent mixture can be a mixture of organic solvents selected from ethylacetate, dimethyl formamide, methanol, ethanol, isopropanol and dichloromethane, preferably the solvent mixture is composed of a mixture of a protic solvent with dichloromethane, more preferably methanol with dichloromethane.

In an embodiment, the acidification of the solvent mixture preferably occurs by absorption of HCl gas.

In an embodiment, the high purity crude compound of formula III or formula II obtained does not require any base neutralization and is promptly recrystallized from water and/or a protic solvent.

One specific embodiment of the present disclosure is a process including the following steps:
placing compound of formula VI, or VIII, in toluene;
adding 50% (w/v) aqueous NaOH at 0-5° C.;
adding a mixture of chloroacetyl chloride in toluene into the combination obtained before at a temperature and for a time sufficient to allow the reaction to occur, in particular at 0-5° C. for 4 hours;
adding water to ice-water cooled reaction mixture obtained in the previous step;
separating the phases, and the aqueous phase is extracted with toluene;
treating the organic phase with an organic or inorganic acid solution and the resulting suspension is filtered, in particular 2M aqueous HCl;
the filtered solid identified as the salt of compound of formula VI, or the salt of compound of formula VIII, is recovered and re-used in the chloroacetylation step;
separating the phases of the mother liquor, and extracting the aqueous phase with toluene;
drying the organic phase, filtering and concentrating under reduced pressure to obtain a mixture of crude compound of formula X, or XI, in toluene;
adding a phase transfer catalyst and 50% (w/v) aqueous sodium hydroxide to the crude product (in particular in toluene) mixture obtained in the previous step at a temperature and for a time sufficient to allow the reaction to occur, in particular at 65° C. for 1 hour;
adding water to the mixture at 0° C. and separating the phases;
washing the organic layer with aqueous HCl and water;
drying the organic layer is dried, filtering and evaporating to give compound of formula IV, or XIV;
placing the compound of formula IV, or compound of formula XIV, in THF;
adding of a mixture of sodium bis(2-methoxyethoxy) aluminium hydride in THF into the THF mixture prepared before at a temperature and for a time sufficient to allow the reaction to occur (additional mixture of sodium bis(2-methoxyethoxy)aluminium hydride in toluene might be required);
adding 5% (w/v) aqueous NaOH, water and DCM;
separating the phases and extracting the aqueous phase with DCM;
drying the organic phase, filtering and evaporating the solvent to give crude product of formula V, or IX;
placing the crude product obtained in the previous step into DCM and adding methanol (MeOH) to obtain compound of formula V, or IX.

The process of the disclosure is suitable for industrial use and presents advantages such as the use of a mixture of acid chloride, in particular acetyl chloride, in a biphasic system made of a mixture of toluene and 50% (w/v) aqueous solution of sodium hydroxide, as an alternative to the unstable mixture of trimethylamine and acid chloride; and also the phase-transfer catalyst load used was very reduced, in particular less than 0.1 equivalents in relation to compound of formula X.

The process of the disclosure also describes the selective reduction of a lactam ring into a piperazine.

In an embodiment, the pharmaceutically accepted salts according to the disclosure include therapeutically active, non-toxic acid salt form which the compounds of formula II and III are able to form.

The acid addition salt form of a compound of formula II and III that occurs in its free form as a base can be obtained by treating the free base with an appropriate acid such as an inorganic acid, for example hydrochloric, hydrobromic, sulphuric, phosphoric, nitric acid and the like; or an organic acid, such as, for example, acetic, citric, citric anhydrous, mandelic, hydroxyacetic, lactic, pyruvic, maleic, malonic, fumaric, malic, methanesulfonic, succinic, tartaric, p-toluenesulfonic, cyclamic, ethanesulfonic, glutamic, 1,2-ethanedisulfonic acid and the like.

In an embodiment, the salt form can be converted into the free form by treatment with base.

In an embodiment, compounds of formula II and III and their salts can be in the form of a solvate, which is included within the scope of the present disclosure. Such solvates include for example hydrates, alcoholates and the like.

In an embodiment, in all the above mentioned scopes the optically active centre can assume both the configuration 'R'- or 'S'.

In an embodiment, compounds formula I, II and III and some intermediates have one or two stereogenic centres in their structure. This stereogenic center may be present in a R or a S configuration, said R and S notation is used in correspondence with the rules described in Pure Applied Chemistry 1976, 45, 11-30.

The disclosure relates to all stereoisomeric forms such as enantiomeric and diastereomeric forms of the compounds of formula I, II and III or intermediates.

The preparation of the compound of formula III starting from compound of formula VII may be performed in a series of separate reactions whereby each intermediate is isolated, or may be performed as a telescopic synthesis.

For the purposes of this disclosure, it is considered as enantiomerically pure when enantiomeric purity is equal to or greater than 97%.

In accordance with the present disclosure, Pirlindole enantiomer II and III produced by the process of the present disclosure may be prepared as pharmaceutical compositions that are particularly useful for the treatment of CNS disorders, in particular depression. Such compositions comprise (R)-Pirlindole II or (S)-Pirlindole III with pharmaceutical carriers and/or excipients known to one of skill in the art.

Example 1—Preparation of (S)-8-methyl-3-((S)-1-phenylethyl)-3a,4,5,6-tetrahydro-1H-pyrazino[3,2,1-jk]carbazol-2(3H)-one—Formula IV

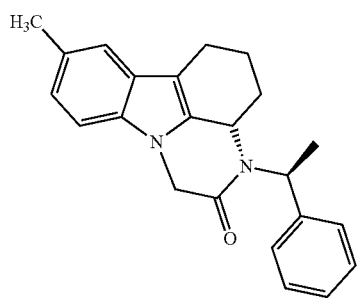

IV

In an embodiment, the preparation of (S)-8-methyl-3-((S)-1-phenylethyl)-3a,4,5,6-tetrahydro-1H-pyrazino[3,2,1-jk]carbazol-2(3H)-one (Formula IV) was carried out as follows. To the solution of VI (S)-6-methyl-N—((S)-1-phenylethyl)-2,3,4,9-tetrahydro-1H-carbazol-1-amine (30 g, 98.5 mmol) in toluene (300 mL), 50% (w/v) aqueous NaOH (79 g) was added dropwise at 0-5° C., then the solution of chloroacetyl chloride (12 mL, 148 mmol, 1.5 equiv.) in toluene (15 mL) was added dropwise at 0-5° C. The mixture was stirred at 0-5° C. for approximately 2.5 h, and additional chloroacetyl chloride (12 mL, 148 mmol, 1.5 equiv.) in toluene (15 mL) was added dropwise at 0-5° C. The mixture was stirred at 0-5° C. for approximately 1.5 h. Water was added to the reaction mixture keeping the temperature below 5° C. The phases were separated, and the aqueous phase was extracted with toluene. The organic phase was treated with 2M aqueous HCl. The resulting suspension was filtered. The filtered solid was identified as the HCl salt of VI, which can be liberated and driven back to the chloroacetylation step. The phases of the mother liquor were separated, and the aqueous phase was extracted with toluene. The organic phase was dried over $Na_2SO_4$, filtered and concentrated under reduced pressure to about 350 mL as a solution in toluene. The toluene solution of the crude product compound of formula X was reacted in the next step.

In an embodiment, in the same reaction vessel to the toluene solution of crude intermediate obtained in previous step were added TBAB (0.394 g, 1.22 mmol, 1 w/w % for the theoretical yield of prev. step) and 50% (w/v) aqueous NaOH (8.1 g, 10 equiv.). The reaction mixture was stirred for 1 h at 65° C., while the reaction was complete. Water was added to the mixture at 0° C., and the phases were separated, the organic phase was washed with aqueous HCl, and with water, then dried over $Na_2SO_4$, filtered and evaporated to give 32.87 g of compound IV (S)-8-methyl-3-((S)-1-phenylethyl)-3a,4,5,6-tetrahydro-1H-pyrazino[3,2,1-jk]carbazol-2(3H)-one (yield: 97% for the two steps) as a brown solid. The crude product was reacted in the next step without further purification.

Example 2—Preparation of (S)-8-methyl-3-((S)-1-phenylethyl)-2,3,3a,4,5,6-hexahydro-1H-pyrazino[3,2,1-jk]carbazole—Formula V

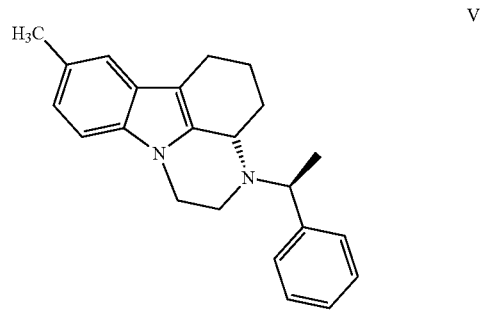

V

In an embodiment, the preparation of (S)-8-methyl-3-((S)-1-phenylethyl)-2,3,3a,4,5,6-hexahydro-1H-pyrazino[3,2,1-jk]carbazole (Formula V) was performed as follows. To the stirred solution of 32.87 g of IV, (S)-8-methyl-3-((S)-1-phenylethyl)-3a,4,5,6-tetrahydro-1H-pyrazino[3,2,1-jk]carbazol-2(3H)-one (95.4 mmol) in dry THF (170 mL) 66 mL solution of sodium bis(2-methoxyethoxy)aluminium hydride in toluene (70 w/w %, 237 mmol, 2.5 equiv.) was added dropwise. The reaction mixture was warmed to 40° C., and the end of the addition the mixture was stirred at 50° C. until the total consumption of the starting material. Additional 22 mL of sodium bis(2-methoxyethoxy)aluminium hydride solution (70 w/w %, 79 mmol, 0.8 equiv.) was added dropwise. After completion the mixture was cooled to room temperature and 5% aqueous NaOH was added carefully. Water and DCM were added to the mixture, the phases were separated, and the aqueous phase was extracted with DCM. The organic phase was dried over $Na_2SO_4$, filtered and the solvent was evaporated to get a brown solid (28.8 g). This crude product was dissolved in DCM and MeOH was added. White solid precipitated. The solid was filtered and washed with MeOH to give V (S)-8-methyl-3-((S)-1-phenylethyl)-2,3,3a,4,5,6-hexahydro-1H-pyrazino[3,2,1-jk]carbazole 14.6 g (yield: 46%) as an off-white cotton-like solid.

Example 3—Preparation of (S)-Pirlindole Hydrochloride—Formula III

In an embodiment, the preparation of (S)-Pirlindole hydrochloride III was carried out as follows. The free amine V ((S)-8-methyl-3-((S)-1-phenylethyl)-2,3,3a,4,5,6-hexahydro-1H-pyrazino[3,2,1-jk]carbazole) (8.32 g, 25 mmol) was dissolved in DCM (42 mL) and excess of HCl in MeOH (42 mL) was added. The solvents were evaporated under reduced pressure to dryness to give a yellow oil. The residue was dissolved in MeOH (120 mL) and was added to the dispersion of Pd/C (1.74 g, ~50% water) in MeOH (20 mL). The reaction mixture was stirred at 50° C. under 750 KPa (7.5 bar) pressure of hydrogen for 5 h. After completion (HPLC) the suspension was filtered through a celite pad, and the filter cake was washed with MeOH. The pH of the resulting solution was checked (<3) and it was evaporated to give the crude hydrochloride salt of compound of formula III. To the crude material iPrOH was added and the suspension was allowed to stir at reflux. The suspensions were filtered, and the product was dried under vacuum to give the hydrochloride salt of (S)-Pirlindole, compound of formula III (5.11 g, 19.5 mmol, yield: 77%). Purity >99.5% (HPLC). Enantiomeric purity 99.5% (Chiral HPLC). MS (ESI): m/z 227.2 (M+H)$^+$.

TABLE 1

Comparative yields

| | N-Acylation Yield (%) | Acetamide cyclisation (Lactam) Yield (%) | Lactam Reduction (Piperazine) Yield (%) | Hydrogenolysis (Pirlindole) Yield (%) |
|---|---|---|---|---|
| Present disclosure | 97 | | 46 | 77 |
| Andreeva et al. 1992 | | 23.8 | | 42 |
| Bokanov et al. 1988 | 81 | 52 | — | — |

Surprisingly, the process of the present disclosure, for the synthesis of pirlindole enantiomers of formula II or III, is responsible for higher individual and global yields than the processes already disclosed in the literature. In particular higher lactam ring formation yield, the present disclosure describes 97% yield while Bokanov et al. reports 42% yield. Higher yields are also observed for the piperazine ring formation, the present disclosure describes 45% yield instead of the 23.8% exhibited by Andreeva et al. The same is observed for the hydrogenolysis, Andreeva et al. unfold 42% yield for Pirlindole salt isolation and the present disclosure describe 77% yield for the same transformation. A further advantage of the process now disclosed is the possibility of removing benzene, a toxic compound, from the catalytic hydrogenolysis. An even further advantage is that the process now disclosed is also safer than, for example, the process disclosed in Andreeva et al. 1992 wherein sodium hydride (NaH) in the presence of dimethyl sulfoxide (DMSO) or dimethyl formamide (DMF) is employed. The process now disclosed is safer because no generating exothermic decomposition arises from said process.

The term "comprising" whenever used in this document is intended to indicate the presence of stated features, integers, steps, components, but not to preclude the presence or addition of one or more other features, integers, steps, components or groups thereof.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

The disclosure should not be seen in any way restricted to the embodiments described and a person with ordinary skill in the art will foresee many possibilities to modifications thereof.

The above described embodiments are combinable.

The following claims further set out particular embodiments of the disclosure.

The invention claimed is:

1. A process for the synthesis of a pharmaceutically acceptable salt of (R)-Pirlindole of formula II:

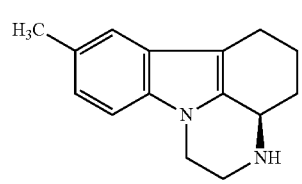

wherein the process comprises the following steps:
1) reacting a compound of formula VIII:

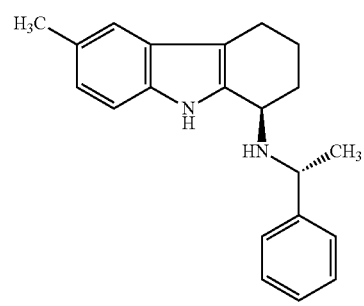

with an acylating compound of formula XII:

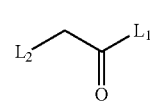

wherein:
L$_1$ is Cl, Br, OR$_1$, OC(O)R$_1$, OS(O)$_2$CH$_3$, OS(O)$_2$-Ph-(CH$_3$), or imidazolyl;
L$_2$ is Cl, Br, I, OR$_1$, OS(O)$_2$CH$_3$, or OS(O)$_2$-Ph-(CH$_3$); and
R$_1$ is H, C$_1$-C$_6$ alkyl, or aryl;
in the presence of a first aprotic solvent and an alkaline agent selected from the group consisting of an alkali metal bicarbonate, an alkali metal carbonate, an alkali metal hydroxide, and a tertiary organic amine, to provide a compound of formula XI:

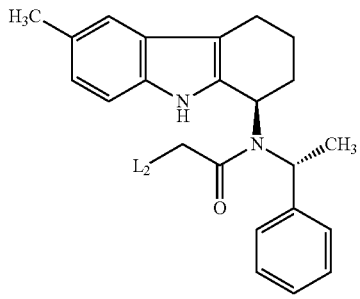

wherein:
L$_2$ is Cl, Br, I, OR$_1$, OS(O)$_2$CH$_3$, or OS(O)$_2$-Ph-(CH$_3$); and
R$_1$ is H, C$_1$-C$_6$ alkyl, or aryl;

2) intramolecularly cyclizing the compound of formula XI above with an alkaline agent selected from the group consisting of an alkali metal bicarbonate, an alkali metal carbonate, an alkali metal hydroxide, and a tertiary organic amine, in the presence of a second aprotic solvent and a quaternary ammonium halide phase transfer catalyst, to provide a compound of formula XIV:

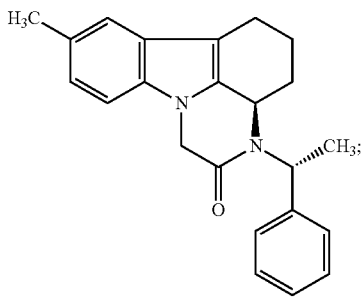

3) reacting the compound of formula XIV above with a reducing agent selected from the group consisting of borane tetrahydrofuran complex, aluminum hydride, diisobutylaluminum hydride, lithium aluminum hydride, and sodium bis(2-methoxyethoxy)aluminum hydride, in the presence of a third aprotic solvent, to provide a compound of formula IX:

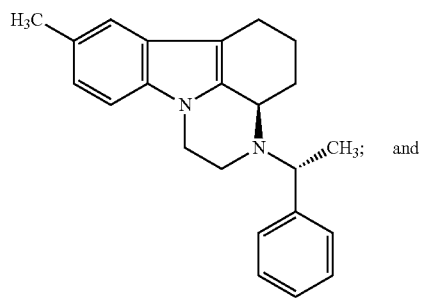

and 4) reacting the compound of formula IX above (a) with an acidic cleavage agent selected from the group consisting of a boron trihalide and an aluminum trihalide, or (b) under catalytic hydrogenolysis comprising hydrogen in the presence of Pd/C, a solvent, and an excess of an acid selected from the group consisting of acetic acid, citric acid, ethanesulfonic acid, glutamic acid, hydrobromic acid, hydrochloric acid, lactic acid, maleic acid, malonic acid, mandelic acid, methanesulfonic acid, phosphoric acid, succinic acid, and tartaric acid, to provide the pharmaceutically acceptable salt of (R)-Pirlindole of formula II above.

2. The process according to claim 1, wherein the pharmaceutically acceptable salt of (R)-Pirlindole of formula II is selected from the group consisting of the acetate salt, the citrate salt, the ethanesulfonate salt, the hydrobromide salt, the hydrochloride salt, the lactate salt, the maleate salt, the malonate salt, the mandelate salt, the methanesulfonate salt, the phosphate salt, the succinate salt, and the tartrate salt.

3. The process according to claim 1, wherein the acylating compound of formula XII is:

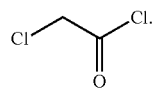

4. The process according to claim 1, wherein the alkaline agent is selected from the group consisting of sodium bicarbonate, potassium bicarbonate, sodium carbonate, potassium carbonate, sodium hydroxide, potassium hydroxide, trimethylamine, and pyridine.

5. The process according to claim 4, wherein the alkaline agent is selected from the group consisting of sodium hydroxide and potassium hydroxide.

6. The process according to claim 1, wherein the alkaline agent in step 1) and step 2) is a 50% (w/v) aqueous solution of sodium hydroxide.

7. The process according to claim 1, wherein the molar ratio of the alkaline agent to the compound of formula VIII to the compound of formula XII is in the range of 1:1:1 to 15:1:4.

8. The process according to claim 1, wherein the molar ratio of the alkaline agent to the compound of formula VIII to the compound of formula XII is 10:1:3.

9. The process according to claim 1, wherein the first aprotic solvent and the second aprotic solvent are independently selected from the group consisting of dichloromethane, chloroform, diethyl ether, dimethoxyethane, and toluene.

10. The process according to claim 1, wherein at least one of the first aprotic solvent and the second aprotic solvent is toluene.

11. The process according to claim 1, wherein the quaternary ammonium halide phase transfer catalyst is selected from the group consisting of tetrabutylammonium bromide, tetraethylammonium bromide, benzyltributylammonium bromide, and benzyltributylammonium chloride.

12. The process according to claim 1, wherein the molar ratio of the alkaline agent to the compound of formula XI to the quaternary ammonium halide phase transfer catalyst is in the range of 1:1:0.005 to 15:1:0.1.

13. The process according to claim 1, wherein the molar ratio of the alkaline agent to the compound of formula XI to the quaternary ammonium halide phase transfer catalyst is 10:1:0.01.

14. The process according to claim 1, wherein the reducing agent is sodium bis(2-methoxyethoxy)aluminum hydride.

15. The process according to claim 1, wherein the molar ratio of the reducing agent to the compound of formula XIV is in the range of 1:1 to 4:1.

16. The process according to claim 1, wherein the molar ratio of the reducing agent to the compound of formula XIV is 3.3:1.

17. The process according to claim 1, wherein the third aprotic solvent is selected from the group consisting of dichloromethane, diethyl ether, tetrahydrofuran, and toluene.

18. The process according to claim 1, wherein the pharmaceutically acceptable salt of (R)-Pirlindole of formula II is formed by reacting the compound of formula IX under catalytic hydrogenolysis comprising hydrogen in the presence of Pd/C.

19. The process according to claim 1, wherein the catalytic hydrogenolysis is performed in the presence of a solvent selected from the group consisting of dichloromethane, dimethylformamide, ethyl acetate, methanol, ethanol, and isopropanol.

20. The process according to claim 1, wherein the catalytic hydrogenolysis is performed at a temperature in the range of 20° C. to 70° C. under a hydrogen pressure in the range of 500 kPa to 2000 kPa over a period of two to eight hours.

21. A process for the synthesis of a pharmaceutically acceptable salt of (S)-Pirlindole of formula III:

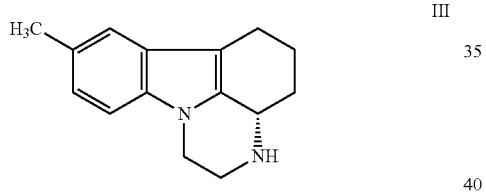

III wherein the process comprises the following steps:
1) reacting a compound of formula VI:

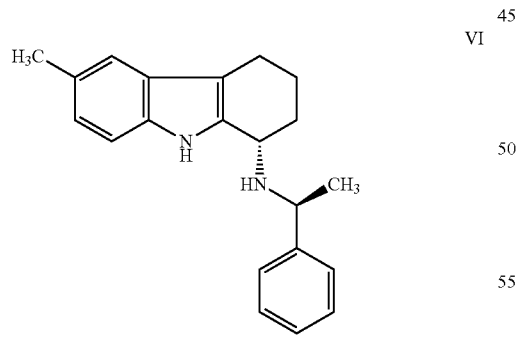

VI with an acylating compound of formula XII:

XII wherein:
$L_1$ is Cl, Br, $OR_1$, $OC(O)R_1$, $OS(O)_2CH_3$, $OS(O)_2$-Ph-$(CH_3)$, or imidazolyl;
$L_2$ is Cl, Br, I, $OR_1$, $OS(O)_2CH_3$, or $OS(O)_2$-Ph-$(CH_3)$; and
$R_1$ is H, $C_1$-$C_6$ alkyl, or aryl;

in the presence of a first aprotic solvent and an alkaline agent selected from the group consisting of an alkali metal bicarbonate, an alkali metal carbonate, an alkali metal hydroxide, and a tertiary organic amine, to provide a compound of formula X:

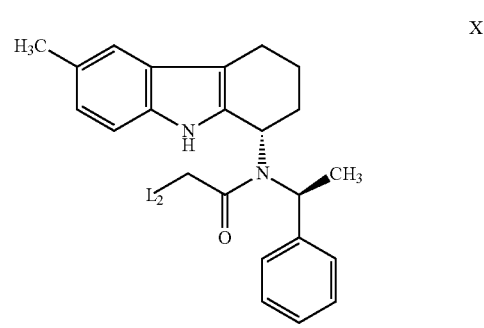

X wherein:
$L_2$ is Cl, Br, I, $OR_1$, $OS(O)_2CH_3$, or $OS(O)_2$-Ph-$(CH_3)$; and
$R_1$ is H, $C_1$-$C_6$ alkyl, or aryl;

2) intramolecularly cyclizing the compound of formula X above with an alkaline agent selected from the group consisting of an alkali metal bicarbonate, an alkali metal carbonate, an alkali metal hydroxide, and a tertiary organic amine, in the presence of a second aprotic solvent and a quaternary ammonium halide phase transfer catalyst, to provide a compound of formula IV:

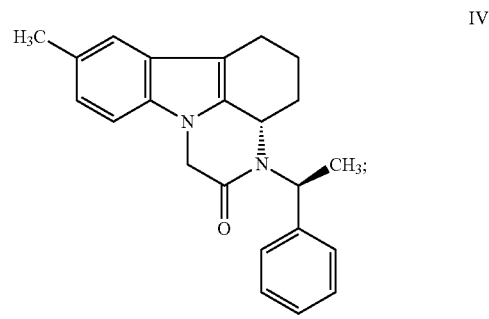 [SMILES: Cc1ccc2c(c1)c1c3n2CC(=O)N([C@@H](C)c2ccccc2)[C@H]3CCC1]

IV 3) reacting the compound of formula IV above with a reducing agent selected from the group consisting of borane tetrahydrofuran complex, aluminum hydride, diisobutylaluminum hydride, lithium aluminum hydride, and sodium bis(2-methoxyethoxy)aluminum hydride, in the presence of a third aprotic solvent, to provide a compound of formula V:

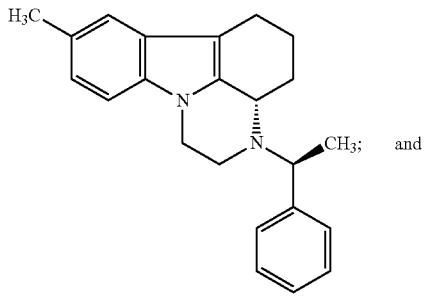

4) reacting the compound of formula V above (a) with an acidic cleavage agent selected from the group consisting of a boron trihalide and an aluminum trihalide, or (b) under catalytic hydrogenolysis comprising hydrogen in the presence of Pd/C, a solvent, and an excess of an acid selected from the group consisting of acetic acid, citric acid, ethanesulfonic acid, glutamic acid, hydrobromic acid, hydrochloric acid, lactic acid, maleic acid, malonic acid, mandelic acid, methanesulfonic acid, phosphoric acid, succinic acid, and tartaric acid, to provide the pharmaceutically acceptable salt of (S)-Pirlindole of formula III above.

22. The process according to claim 21, wherein the pharmaceutically acceptable salt of (S)-Pirlindole of formula III is selected from the group consisting of the acetate salt, the citrate salt, the ethanesulfonate salt, the hydrobromide salt, the hydrochloride salt, the lactate salt, the maleate salt, the malonate salt, the mandelate salt, the methanesulfonate salt, the phosphate salt, the succinate salt, and the tartrate salt.

23. The process according to claim 21, wherein the acylating compound of formula XII is:

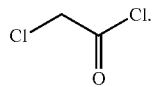

24. The process according to claim 21, wherein the alkaline agent is selected from the group consisting of sodium bicarbonate, potassium bicarbonate, sodium carbonate, potassium carbonate, sodium hydroxide, potassium hydroxide, trimethylamine, and pyridine.

25. The process according to claim 24, wherein the alkaline agent is selected from the group consisting of sodium hydroxide and potassium hydroxide.

26. The process according to claim 21, wherein the alkaline agent in step 1) and step 2) is a 50% (w/v) aqueous solution of sodium hydroxide.

27. The process according to claim 21, wherein the molar ratio of the alkaline agent to the compound of formula VI to the compound of formula XII is in the range of 1:1:1 to 15:1:4.

28. The process according to claim 21, wherein the molar ratio of the alkaline agent to the compound of formula VI to the compound of formula XII is 10:1:3.

29. The process according to claim 21, wherein the first aprotic solvent and the second aprotic solvent are independently selected from the group consisting of dichloromethane, chloroform, diethyl ether, dimethoxyethane, and toluene.

30. The process according to claim 21, wherein at least one of the first aprotic solvent and the second aprotic solvent is toluene.

31. The process according to claim 21, wherein the quaternary ammonium halide phase transfer catalyst is selected from the group consisting of tetrabutylammonium bromide, tetraethylammonium bromide, benzyltributylammonium bromide, and benzyltributylammonium chloride.

32. The process according to claim 21, wherein the molar ratio of the alkaline agent to the compound of formula X to the quaternary ammonium halide phase transfer catalyst is in the range of 1:1:0.005 to 15:1:0.1.

33. The process according to claim 21, wherein the molar ratio of the alkaline agent to the compound of formula X to the quaternary ammonium halide phase transfer catalyst is 10:1:0.01.

34. The process according to claim 21, wherein the reducing agent is sodium bis(2-methoxyethoxy)aluminum hydride.

35. The process according to claim 21, wherein the molar ratio of the reducing agent to the compound of formula IV is in the range of 1:1 to 4:1.

36. The process according to claim 21, wherein the molar ratio of the reducing agent to the compound of formula IV is 3.3:1.

37. The process according to claim 21, wherein the third aprotic solvent is selected from the group consisting of dichloromethane, diethyl ether, tetrahydrofuran, and toluene.

38. The process according to claim 21, wherein the pharmaceutically acceptable salt of (S)-Pirlindole of formula III is formed by reacting the compound of formula V under catalytic hydrogenolysis comprising hydrogen in the presence of Pd/C.

39. The process according to claim 21, wherein the catalytic hydrogenolysis is performed in the presence of a solvent selected from the group consisting of dichloromethane, dimethylformamide, ethyl acetate, methanol, ethanol, and isopropanol.

40. The process according to claim 21, wherein the catalytic hydrogenolysis is performed at a temperature in the range of 20° C. to 70° C. under a hydrogen pressure in the range of 500 kPa to 2000 kPa over a period of two to eight hours.

* * * * *